(12) United States Patent
Metcalfe

(10) Patent No.: US 9,216,090 B2
(45) Date of Patent: Dec. 22, 2015

(54) JOINT IMPLANT TRIAL COMPONENTS

(71) Applicant: Arthrex, Inc., Naples, FL (US)

(72) Inventor: Nick Metcalfe, Gräfelfing (DE)

(73) Assignee: Arthrex, Inc., Naples, FL (US)

( * ) Notice: Subject to any disclaimer, the term of this patent is extended or adjusted under 35 U.S.C. 154(b) by 108 days.

(21) Appl. No.: 13/803,201

(22) Filed: Mar. 14, 2013

(65) Prior Publication Data
US 2013/0245775 A1 Sep. 19, 2013

(30) Foreign Application Priority Data

Mar. 15, 2012 (EP) .................................... 12159757

(51) Int. Cl.
A61F 2/40 (2006.01)
A61F 2/46 (2006.01)
A61F 2/30 (2006.01)

(52) U.S. Cl.
CPC ................. *A61F 2/40* (2013.01); *A61F 2/4059* (2013.01); *A61F 2/4684* (2013.01); *A61F 2002/305* (2013.01); *A61F 2002/3055* (2013.01); *A61F 2002/30331* (2013.01); *A61F 2002/30367* (2013.01); *A61F 2002/30594* (2013.01); *A61F 2002/30616* (2013.01); *A61F 2002/4022* (2013.01); *A61F 2002/4062* (2013.01); *A61F 2002/4641* (2013.01)

(58) Field of Classification Search
CPC ..... A61F 2/4612; A61F 2/581; A61F 2/4014; A61F 2002/4022; A61F 2002/4025; A61F 2002/4037; A61F 2002/4074; A61F 2/40; A61F 2/4081; A61F 2002/347; A61F 2002/3472; A61F 2002/3474; A61F 2002/3477

USPC .................. 623/18.11, 19.11–19.14
See application file for complete search history.

(56) References Cited

U.S. PATENT DOCUMENTS

| 4,135,517 | A | | 1/1979 | Reale |
| 5,019,105 | A | * | 5/1991 | Wiley ......................... 623/22.29 |
| 5,156,626 | A | | 10/1992 | Broderick et al. |
| 6,776,799 | B2 | * | 8/2004 | Ball et al. .................... 623/19.11 |
| 6,926,740 | B2 | * | 8/2005 | Lewis et al. ................. 623/22.28 |
| 7,044,975 | B2 | * | 5/2006 | Cheal et al. ................. 623/22.42 |
| 7,819,923 | B2 | | 10/2010 | Stone et al. |
| 2007/0250175 | A1 | | 10/2007 | Meridew et al. |
| 2009/0210065 | A1 | | 8/2009 | Nerot et al. |

FOREIGN PATENT DOCUMENTS

| EP | 2 047 827 A1 | 4/2009 |
| FR | 2 773 469 A1 | 7/1999 |
| WO | WO 2007/084939 A2 | 7/2007 |

* cited by examiner

Primary Examiner — Anu Ramana
(74) Attorney, Agent, or Firm — Dickstein Shapiro LLP

(57) ABSTRACT

A humeral component of a prosthesis comprises a stem module for fixing the prosthesis into a bone. A joint adapter can be attached, preferably under different angles to the stem module. The joint adapter holds a liner having a recessed spherical cavity, which is the cup of the joint. The joint adapter has an inner surface and a circumferential groove. The liner has an outer surface including a circular recess. This circular recess preferably is concentric to the major body diameter of the liner for interfacing with the circumferential groove of the joint adapter. Furthermore, the liner has a radial slit, which allows compression of the liner for easy insertion and removal. This allows inserting different liners with different sizes thus allowing to try out different sizes to find the best size for the patient. When the best size has been identified, a final liner without a slit may be inserted.

13 Claims, 5 Drawing Sheets

JOINT IMPLANT TRIAL COMPONENTS

PRIORITY CLAIM

This application claims priority to pending European Application No. 12159757 filed on 15 Mar. 2012.

BACKGROUND OF THE INVENTION

1. Field of the Invention

The invention relates to trial components for joint implants and prosthesis, in particular to trial components for shoulder implants and prosthesis.

2. Description of Relevant Art

The shoulder joint is a ball-and-socket joint, which has an exceptional range of motion. Shoulder instability and other maladies of the shoulder joint, such as arthrosis or fracture, may require a replacement of the joint. Also, other joints other than a shoulder joint may require a replacement.

A shoulder joint prosthesis, which includes the replacement of the convex head of the humerus, is disclosed in U.S. Pat. No. 7,819,923. It reflects the orientation and the center of rotation of actual joints. In the case of a worn or damaged rotator cuff or too much bone loss, such a prosthesis would not recover the range of motion. In such a case, a reverse shoulder prosthesis may be preferable. An example of such a prosthesis is disclosed in the US patent application publication 2009/0210065 A1. In such a prosthesis the humeral component includes a stem and a cup attached to the stem. The glenoid component supports a convex head, which articulates with the cup of the humeral component.

In general, the geometry of the prosthesis has to be adjusted to the patient's needs. This may be done by inserting trial liners into the socket part of the joint. The European patent application EP 2 047 827 A1 discloses an expandable trial component which can be adjusted by rotation. It allows a precise adjustment in size, but the reproducibility is poor, as the height cannot precisely be reconstructed after the trial component has been removed from the joint.

The international patent application publication WO 2007/084939 discloses to provide a plurality of trial or provisional articulating liners, which lack spring fingers for fixing the liner to the stem, but otherwise are substantially identical to the implanted articulating liner. Due to the lacking spring fingers these trial liners often wobble, piston or pivot out of position during trail reduction of a joint. Therefore, the surgeon does not obtain a true representation of the new joint and can get a false message during this critical operative step.

SUMMARY OF THE INVENTION

The embodiments are based on the object of designing a trial component for joint implants and prosthesis, in particular for trial components for shoulder implants and prosthesis, which can easily be inserted and removed, but which are still securely held in position during trial.

The trial component of a prosthesis preferably has an outer surface including at least one recess for interfacing with at least one groove of a joint adapter. Most preferably the at least one recess is a circumferential recess at an outer surface of the trial component, which is adapted to fit into a circumferential groove of the inner surface of the joint adapter. The trial component has at least one approximately radially oriented slit, which allows compression of the trial component for easy insertion and removal of the trial component into the joint adapter. Before inserting the trial component into the joint adapter, the trial component may be compressed, so that the width of the at least one approximately radial slit is reduced, therefore reducing the width or the radius of the recess, so it can easily be inserted into the groove of the joint adapter. The trial component may also have a ramp shaped outer surface, which allows snapping of the trial component into the joint adapter. This may result in a clicking noise and/or vibration, giving the surgeon a feedback, that the trial component has securely been locked within the joint adapter. For removal of the trial component, it is compressed, so that the width of the at least one approximately radial slit is reduced and therefore the width or the radius of the recess is reduced which allows removal of the trial component from the joint adapter. Preferably, the trial component is a liner of the joint, which may have a recessed spherical cavity. Furthermore, the trial component may be a spacer, which may be inserted between the joint adapter and the liner. In a further embodiment, the trial components may be a set of liners and spacers.

A further embodiment relates to a joint prosthesis, preferably to the humeral component of a shoulder prosthesis, although the embodiment may be applied to any other kind of prosthesis. A stem module is provided for fixing the prosthesis into the bone. A joint adapter can be attached, preferably under different angles to the stem module. The joint adapter must not necessarily be a separate part. It may also be one part with the stem module. In an alternative embodiment, the joint adapter may be directly mounted, e.g. screwed into the bone. The joint adapter holds a liner preferably having a recessed spherical cavity, which is the cup of the joint. The joint adapter has an inner surface and at least one preferably circumferential groove. The liner has an outer surface including at least one preferably circular recess. This recess preferably is concentric to the major body diameter of the liner. Its purpose is to interface with the at least one groove of the joint adapter or a spacer. Furthermore, the liner is a trial component, which has an approximately radial slit, which allows compression of the liner for easy insertion into the joint adapter or spacer and removal therefrom. This allows inserting different trial liners with different sizes thus allowing to try out different sizes to find the best size for the patient. Furthermore, an optional spacer may be inserted between the liner and the joint adapter. Like the joint adapter, the spacer has an inner surface and at least one preferably circumferential groove for interfacing with the liner. Furthermore, it has an outer surface including at least one preferably circular recess. This recess preferably is concentric to the major body diameter of the liner. Its purpose is to interface with the at least one groove of the joint adapter. Furthermore, the spacer has an approximately radial slit, which allows compression of the spacer for easy insertion into the joint adapter and removal therefrom. This allows inserting different spaces with different sizes, thus allowing to try out different sizes to find the best size for the patient. When the best sizes of the spacer and the liner have been identified a final liner and an optional final spacer without a slit may be inserted, which can no more be removed.

Furthermore, the trial components can be used with both trial cups and definitive implants (cup and spacer) to allow a second trial reduction step.

According to a further embodiment the trial component and/or the liner and/or the spacer has a plurality of slits for increasing flexibility and decreasing compression force to allow for simplified insertion and removal.

According to another embodiment the trial component and/or the liner and/or the spacer has at least one hole, preferably two holes, for inserting a tool which allows compression of the trial component and/or the liner. Most preferably, the tool comprises a pair of pliers.

It is further preferred, if the trial component and/or the liner and/or the spacer has means for preventing rotation within the joint adapter. Such means may be protrusions and/or recesses interfacing with recesses and/or protrusions of the joint adapter.

A further object of the invention is to provide a kit of trial components having different heights. In an alternative embodiment, the trial components may also have their recessed spherical cavity at different radial offsets compared to the joint adapter, therefore providing different eccentricities and/or positions. Furthermore different spacers my may be provided to adapt for different heights.

Another object of the invention is a method for optimizing the joint distance, preferably of a shoulder joint. After inserting a stem module, holding a joint adapter into the bone, at least one trial component of a liner as disclosed above is inserted into the joint adapter and the joint distance is measured and/or tested. The trial component is then removed from the joint adapter by compression of the trial component and pulling the trial component out of the joint adapter. If required, further trial components may be tried out. After the correct liner size has been identified, a final liner, which can no more be removed, is inserted into the stem module.

BRIEF DESCRIPTION OF THE DRAWINGS

In the following, the invention will be described by way of example, without limitation of the general inventive concept, on examples of embodiment and with reference to the drawings.

FIG. 8 shows a liner, which can be snapped in.

Figure 1:
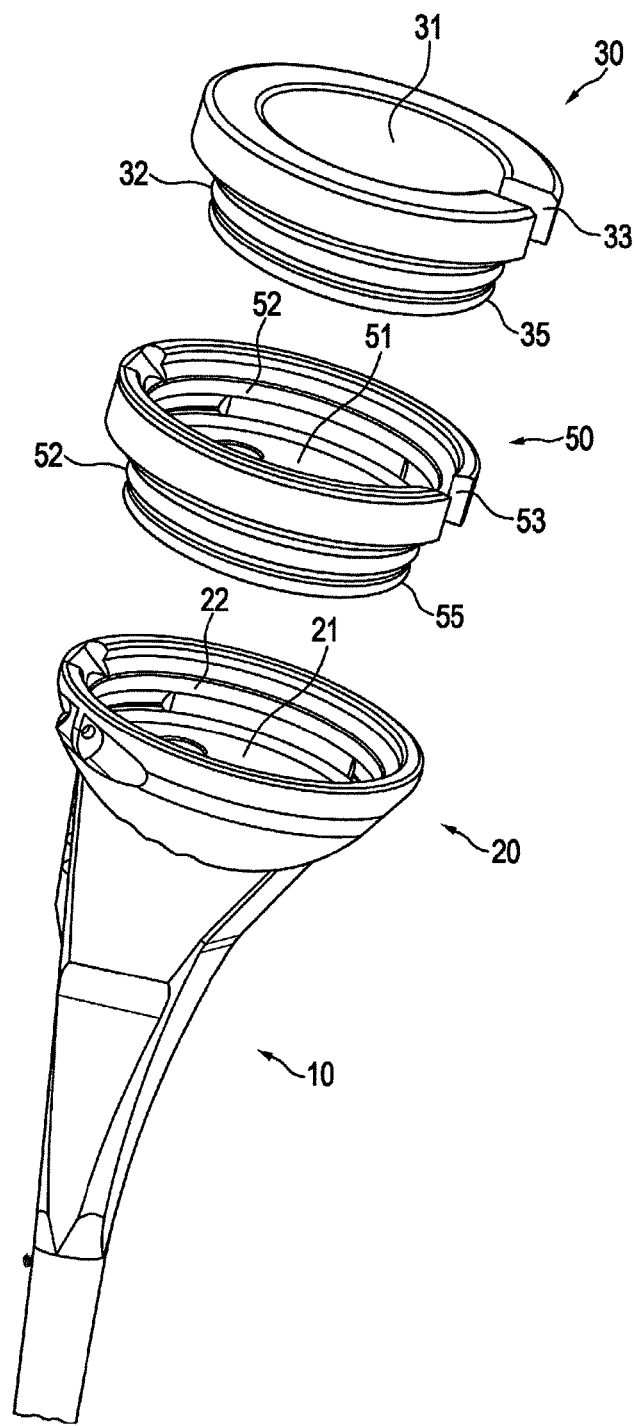
FIG. 1 shows a preferred embodiment.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Figure 2:
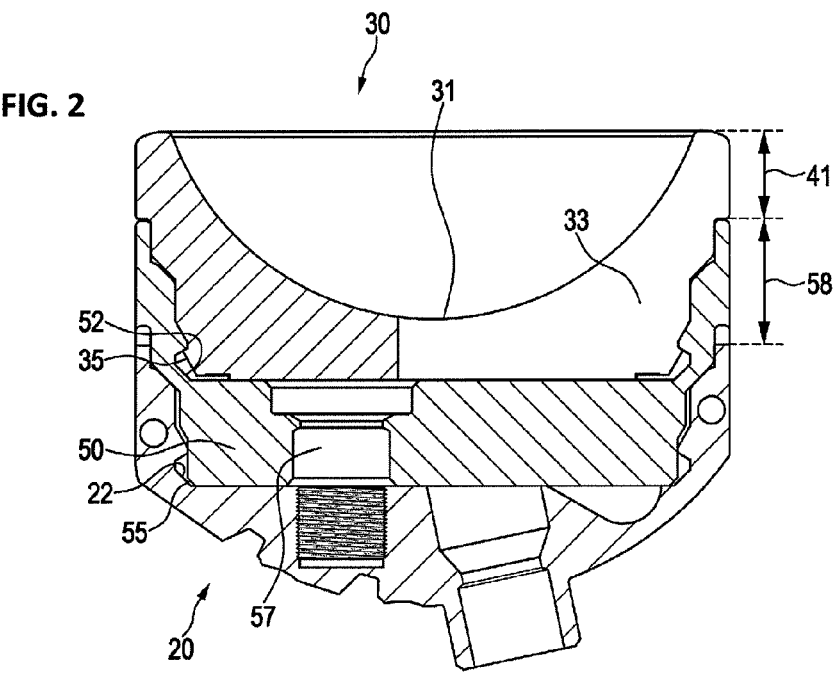
FIG. 2 shows a joint adapter and a liner in more detail.

In FIG. 1, a preferred embodiment is shown. It shows the humeral component of a shoulder prosthesis, although the embodiment may be applied to any other kind of prosthesis. A stem module 10 is provided for fixing the prosthesis into the bone. A joint adapter 20 can be attached, preferably under different angles to the stem module 10. The joint adapter must not necessarily be a separate part. It may also be one part with the stem module. The joint adapter holds a liner 30 preferably having a recessed spherical cavity 31, which is the cup of the joint. The joint adapter 20 has an inner surface 21 and at least one preferably circumferential groove 22. The liner 30 has an outer surface 32 including at least one preferably circular recess 35. This recess preferably is concentric to the major body diameter of the liner. Its purpose is to interface with the at least one groove 22 of the joint adapter 20 or a spacer 50. Furthermore, the liner has an approximately radial slit 33, which allows compression of the liner for easy insertion into the joint adapter 20 or spacer 50 and removal therefrom. This allows inserting different liners with different sizes 41, as shown in FIG. 2, thus allowing to try out different sizes to find the best size for the patient. Furthermore, an optional spacer 50 may be inserted between the liner 30 and the joint adapter 20. Like the joint adapter, the spacer 50 has an inner surface 51 and at least one preferably circumferential groove 52 for interfacing with the liner 30. Furthermore, it has an outer surface 56 including at least one preferably circular recess 55. This recess preferably is concentric to the major body diameter of the liner. Its purpose is to interface with the at least one groove 22 of the joint adapter 20. Furthermore, the spacer has an approximately radial slit 53, which allows compression of the spacer for easy insertion into the joint adapter 20 and removal therefrom. This allows inserting different spaces with different sizes 58, as shown in FIG. 2, thus allowing to try out different sizes to find the best size for the patient. When the best sizes of the spacer and the liner have been identified, a final liner without a slit 33 and an optional final spacer may be inserted, which can no more be removed.

In FIG. 2, a joint adapter 20 with a spacer 50 inserted into the adapter and a liner 30 inserted therein is shown in detail. The liner 30 has a circular recess 35 interfacing with a circumferential groove 52 of spacer 50. The spacer has a circular recess 55 interfacing with a circumferential groove 22 of the joint adapter 20. The spacer furthermore has a screw hole 57 through which a screw may be inserted to fix the spacer to the joint adapter 20. The liner has a height 41. The spacer has a height 58. A kit of trial components may comprise a plurality of liners having different heights 41.

Figure 3:
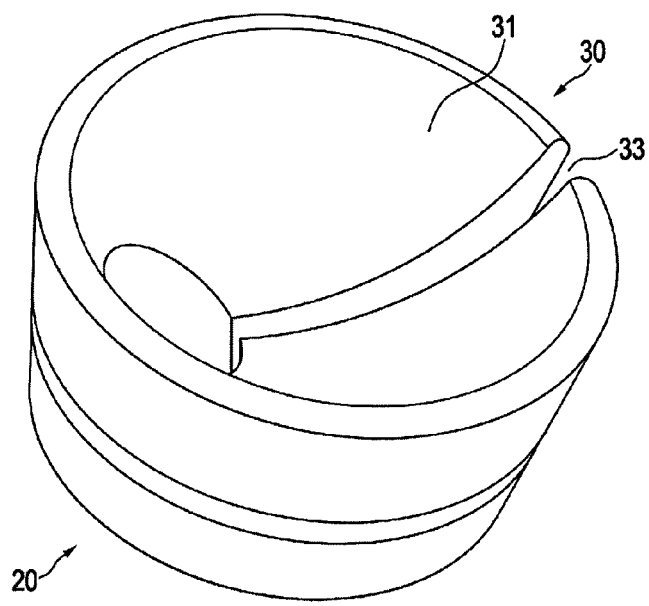
FIG. 3 shows a joint adapter of a liner in a perspective view.

In FIG. 3, a joint adapter 20 together with a liner 30 is shown in perspective view.

Figure 4:
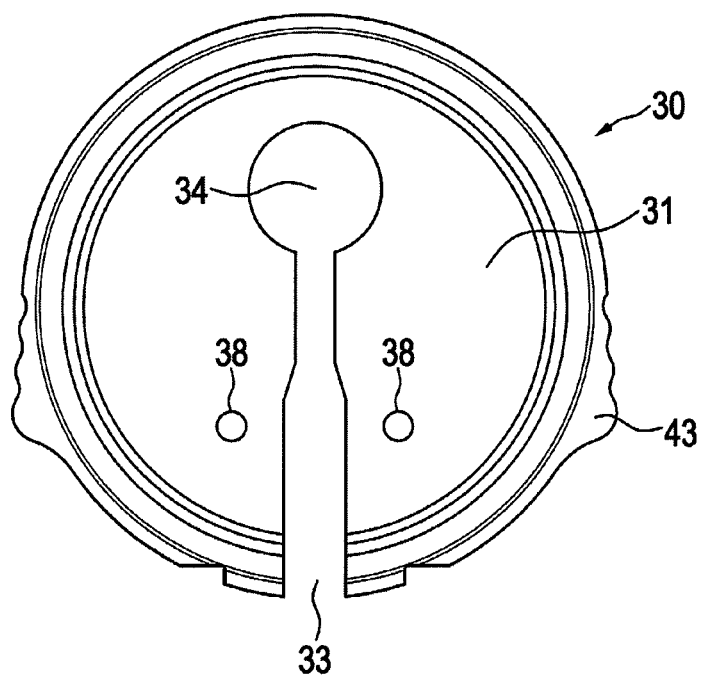
FIG. 4 shows a liner in top view.

In FIG. 4, a liner 30 is shown in the top view. Here the slit 33 is modified to have a larger width towards the outside to allow for more compression. Furthermore, a hole 34 is provided at the end of the slit 33 to improve flexibility and to reduce tensions within the material of the liner. The holes 38 may be used to insert the pair of pliers for compressing the liner, preferably when it has been inserted into the joint adapter. Preferably at least one grip 43, most preferably two grips 43 are provided for compression of the liner and therefore to simplify insertion and removal.

Figure 5:
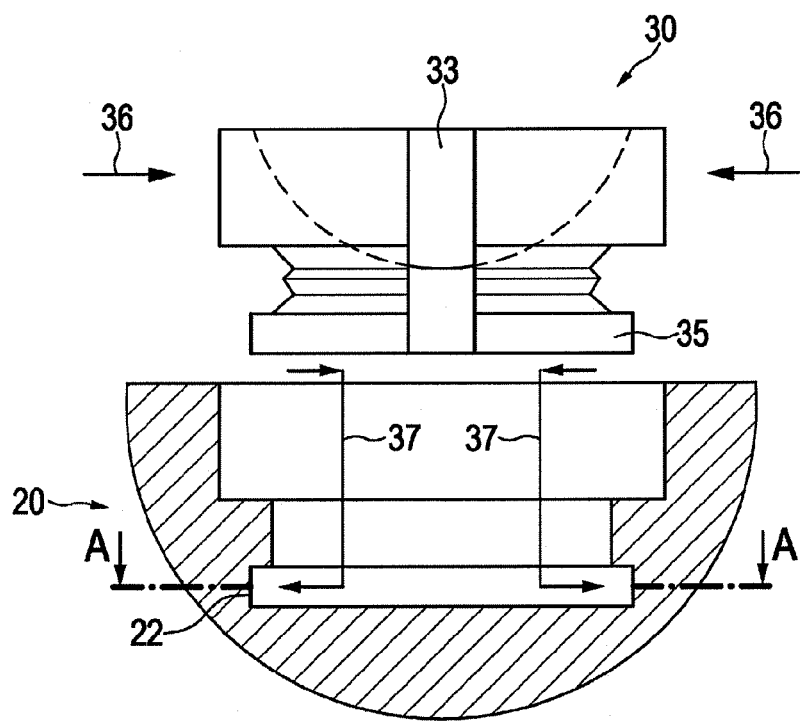
FIG. 5 shows a liner and its insertion in sectional view.

In FIG. 5 a liner 30 and a joint adapter 20 are shown in sectional view. Before insertion or removal, force 36 is applied as shown to the sides of the liner for compression of the liner and therefore allowing to move the circular recess 35 of the liner along a path 37 into the joint adapter 20 so that the circular recess 35 interfaces with circumferential groove 22 of the joint adapter.

Figure 6:
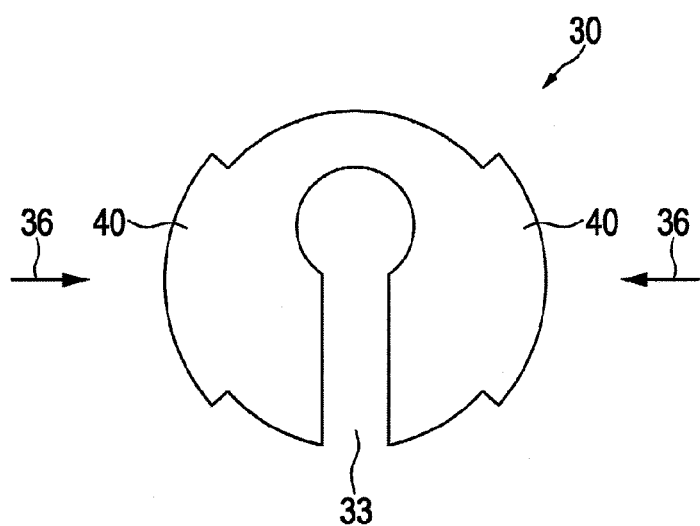
FIG. 6 shows a sectional view of a liner.

In FIG. 6 a sectional view A-A of a liner 30 is shown. It can be seen, how force 36 is applied from the sides. Furthermore, there are arc shaped recess sections 40, which may interface with corresponding sections of the joint adapter (not shown here) and prevent a rotation of the liner relative to the joint adapter.

Figure 7:
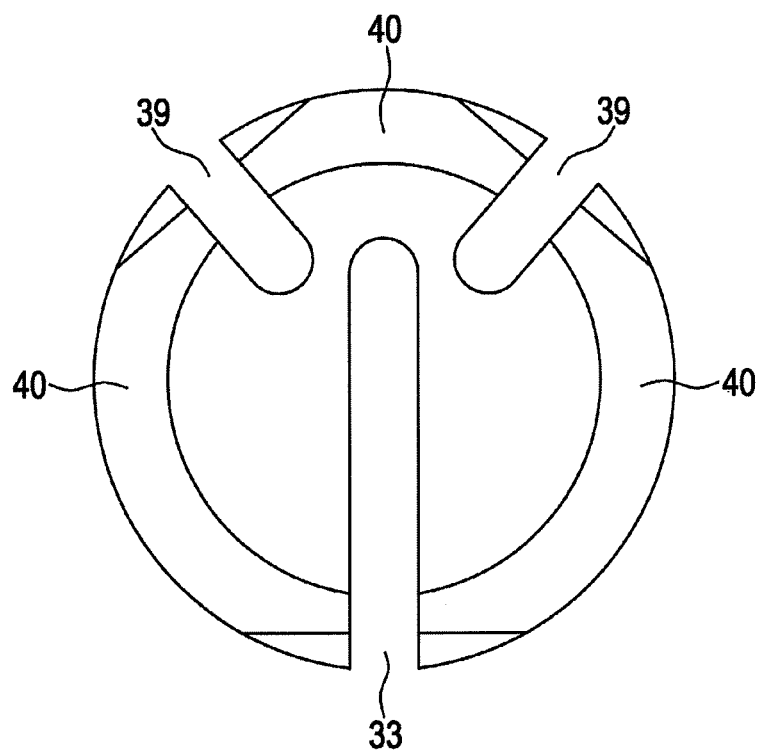
FIG. 7 shows a modified liner with multiple slits.

FIG. 7 shows a modified liner with multiple slits 33, 39. These multiple slits increase flexibility and therefore decrease the force, which is required to compress the liner for insertion and/or removal.

Figure 8:
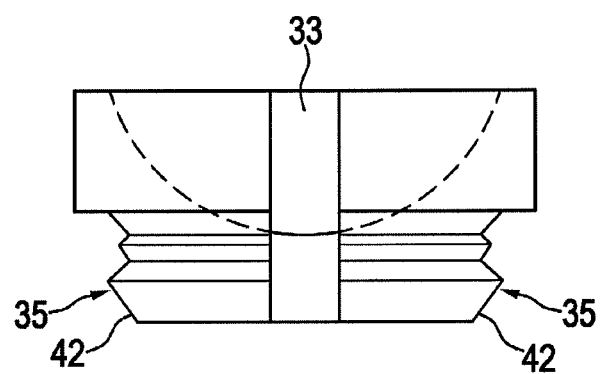

FIG. 8 shows a liner, which can be snapped in. For this purpose, at least one ramp 42 is provided preferably at the bottom side of recess 35.

It will be appreciated to those skilled in the art having the benefit of this disclosure that this invention is believed to provide trial components for joint implants and prosthesis. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

LIST OF REFERENCE NUMERALS 10 stem module
20 joint adapter
21 inner surface
22 circumferential grooves
30 liner
31 recessed spherical cavity
32 outer surface
33 slit
34 hole
35 circular recess
36 force
37 path of movement for insertion.
38 holes for tool
39 slit
40 arc shaped recess sections
41 liner size
42 ramp
50 spacer
51 inner surface
52 circumferential grooves
53 slit
55 circular recess
56 outer surface
57 screw hole
58 spacer size

The invention claimed is:

1. Trial component of a prosthesis, the trial component having an outer surface including at least one recess for interfacing with at least one groove of a joint adapter which can be attached to a stem module or anchored within a bone, wherein the trial component has a radially oriented slit which allows compression of the trial component for easy insertion and removal into the joint adapter,
   wherein the trial component is a liner which has a recessed concave spherical cavity, a concave inner surface, and a thickness, wherein the recessed spherical cavity acts as a cup of a patient's humeral joint, and wherein the radially oriented slit extends through the thickness of the liner, the radially oriented slit extending from a bottom surface to a top surface of the liner, and across a majority of a diameter of a circle in a top view of the concave inner surface of the liner.

2. Trial component according to claim 1, further comprising a spacer which can be inserted between the stem module and the liner and has an inner surface and at least one groove that interfaces with the liner.

3. Trial component according to claim 1, wherein the trial component has a plurality of slits.

4. Trial component according to claim 1, wherein the trial component has at least one ramp for clicking the liner into the joint adapter.

5. Trial component according to claim 1, wherein the trial component has at least one hole for inserting a pair of pliers for compression of the trial component.

6. Trial component according to claim 1, wherein the trial component has at least one protrusion for preventing rotation within the joint adapter.

7. Kit of trial components according to claim 1, wherein the kit comprises a plurality of trial components having different heights.

8. Trial component prosthesis comprising a stem module, and a joint adapter which can be attached to the stem module or anchored within a bone, and a trial component in the form of a liner, the joint adapter having an inner surface and at least one groove, the liner having a recessed concave spherical cavity, a concave inner surface, and a thickness, wherein the recessed spherical cavity acts as a cup of a patient's humeral joint, the liner further having a recessed outer surface including at least one recess for interfacing with the at least one groove of the joint adapter, wherein the liner has a radially oriented slit extending through the thickness of the liner, the radially oriented slit extending from a bottom surface to a top surface of the liner, and across a majority of a diameter of a circle in a top view of the concave inner surface of the cavity.

9. Trial component prosthesis according to claim 8, further comprising a spacer inserted between the stem module and the liner.

10. Trial component prosthesis according to claim 9, wherein the spacer has a radial slit.

11. Trial component prosthesis according to claim 9, wherein the liner or the spacer has at least one ramp for clicking the liner into the joint adapter.

12. Trial component prosthesis according to claim 9, wherein the liner or the spacer has at least one hole for inserting a pair of pliers for compression of the liner.

13. Trial component prosthesis according to claim 9, wherein the liner or the spacer has at least one protrusion for preventing rotation within the joint adapter.

\* \* \* \* \*